United States Patent [19]

Fowler

[11] 4,152,056
[45] May 1, 1979

[54] FINGERPRINTING ARRANGEMENT

[76] Inventor: Randall C. Fowler, 429 Via Los Miradores, Redondo Beach, Calif. 90277

[21] Appl. No.: 830,068

[22] Filed: Sep. 2, 1977

[51] Int. Cl.² .......................... A61B 5/10; G03B 29/00
[52] U.S. Cl. .......................................... 354/62; 355/47
[58] Field of Search ............................. 354/62; 355/47

[56] References Cited

U.S. PATENT DOCUMENTS 3,529,520  9/1970  Thiebault .............................. 354/62

*Primary Examiner*—Russell E. Adams
*Attorney, Agent, or Firm*—Don B. Finkelstein

[57] ABSTRACT

Skin ridge pattern recording apparatus for obtaining and recording skin ridge patterns. A cylindrical transparent element is provided with a central cylindrical bore which, reflects internally. The finger is placed in the bore for producing the skin ridge patterns. The cylindrical element is mounted on a vertical column or post upstanding from a platform which carries a light source projecting a beam of light to the cylindrical element. The light source and a sensitive camera film are carried on a platform which is rotatable with respect to the cylindrical element in which the finger is inserted. The film plane of the camera remains in a fixed relationship with respect to the reflected light from the light source, the angle of incidence being determined by the position of the light source relative to the cylindrical element. The platform is motor driven so that the light source and the film plane of the camera rotate around the cylindrical element to produce the recordation of the skin ridge pattern.

10 Claims, 12 Drawing Figures

FINGERPRINTING ARRANGEMENT

BACKGROUND OF THE INVENTION

1. Field of the Invention

The invention is an apparatus for obtaining and recording skin ridge patterns and, as such, is an apparatus for optically producing and recording photographically finger prints. Particularly, the apparatus is capable of producing skin ridge patterns, that is, finger prints, by transmitting images of the finger prints to a plain optical surface.

2. Description of the Prior Art

The field of invention is that related to what is known in the art as the signalment identified with the art of dactylography, or finger printing. In the prior art, of course, it had been customary to use a method wherein ink or other similar material is applied to the fingers, palms or feet of the individual from which an imprint was taken, the ridge pattern subsequently being transferred by contact printing methods. These techniques of finger printing of course, are subject to many deficiencies and inconveniences. A detailed descrpition of this art may be found for example, in U.S. Pat. Nos. 3,174,414 and 3,282,152 of Meyer and the descriptions of the art in these patents is hereby incorporated herein by reference.

Attempts have been made in the prior art to realize successfull finger printing techniques and apparatus whereby skin ridge patterns could be optically transferred to a film plate and recorded but prior art techniques and apparatus have left much to be desired. Among known prior art patents and publications may be included the following, French patent No. 38249; IBM technical disclosure bulletin volume 8, No. 3, August 1965; U.S. Pat. Nos. 3,138,059; 3,200,701; 3,533,823; 3,482,498; 3,529,520.

With respect to the prior art it would appear that U.S. Pat. No. 3,529,520 of Thiebault is the most pertinent.

A detailed background with respect to the art of finger printing, known as dactylography is given in U.S. Pat. No. 3,174,414 and also in U.S. Pat. No. 3,282,152.

U.S. Pat. No. 3,482,498 has some relevancy but it does not appear to be as pertinent as the U.S. Pat. No. 3,529,520. This patent shows a cylindrical or bell shaped member having an opening or bore through it with curved portions for receiving fingers of different sizes. An optical system is provided which is mounted for rotation about the axis of the cylinder, that is, the finger support. A system of prisms is provided whereby images of the finger are transferred to a photographic film, which is wrapped around a corresponding cylindrical photographic film support.

SUMMARY OF THE INVENTION

The invention relates to an improved technique and apparatus for optically obtaining and recording skin ridge patterns. In the preferred exemplary form of the invention, as described in detail herein, the apparatus is capable of introducing and recording accurate skin ridge patterns of the human finger, that is, finger prints. A cylindrical transparent element having a circular bore is used which provides internal reflection and into which the finger is inserted for the purpose of producing skin ridge patterns, as described more in detail hereinafter. The finger receiving element is carried in an upright post or column upstanding from a circular rotatable platform which is motor driven. Carried on the platform is a light source embodying a slit for transmitting a beam of incident light to the transparent circular finger receiving element. The image of the skin ridge pattern is reflected to a lens forming a part of a camera having a film carrier and a film transport for advancing the film at a predetermined rate. The rotary platform carrying the light source and the sensitive film plate is rotated with respect to the cylindrical element in which the finger is inserted so that the image of the skin ridge pattern is transmitted to the plane of the sensitive film plate which is rotating and advancing so that it is being transported relatively at a corresponding speed to produce an accurate recorded image of the finger print pattern.

In light of the foregoing, the primary object of the invention is to provide an improved aparatus and technique for the purposes outlined and which particularly embodies improved capabilities of projecting the image of the skin ridge pattern to the plane of the sensitized plate.

A further object is to realize improvements in the aparatus and technique by way of providing apparatus wherein a fixed relationship is maintained between the angles of incidence and reflections of light which focuses on the finger to be recorded as well as the sensitive film plate, the aparatus being constructed to carry the light source and the sensitive film plate on a platform which rotates around the finger receiving element.

BRIEF DESCRIPTION OF THE DRAWING

Many further and additional objects and advantages of the invention will become apparent from the following detailed description and on annexed drawings wherein.

DESCRIPTION OF THE PREFERRED EMBODIMENT

Figure 1:
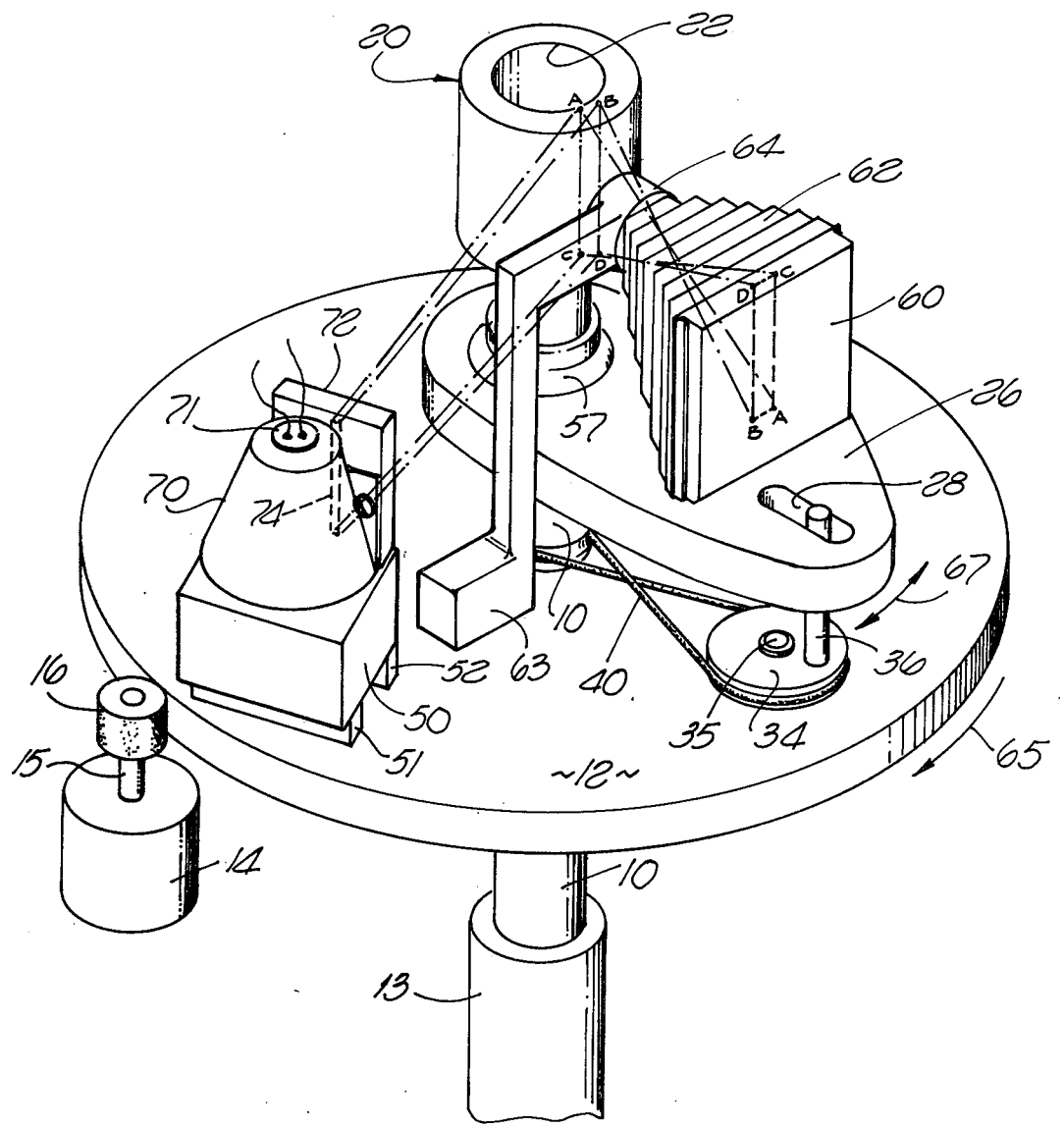
FIG. 1 is a diagramatic perspective view of a preferred form of the invention.

Referring now and more particularly to the various Figures, of the drawings, and especially FIGS. 1 through 5, the perspective view of FIG. 1 shows an upstanding cylindrical post or column 10 telescoped into a cylindrical support member 13. Column 10 carries a circular platform 12 which can be driven in rotation by motor 14 having a shaft 15 on which is a drive pully 16 that frictionally engages one edge of platform 12 for rotating it for purposes which will be described more in detail presently.

Carried at the upper end of column 10, as may be seen in FIG. 1, is a cylindrical transparent finger receiver 20 having a cylindrical center bore 22 into which a finger may be inserted. The inside of the bore 22 is appropriately surfaced to provide reflection of incident light with a predetermined angle of incidence and reflection, as will be referred to in more detail presently. Number 26 designates a secondary platform which is of oval shape as shown and through which the column 10 extends as shown. Platform 26 is mounted for relative angular movement with respect to the column 10 as will be described. Number 28 designates an elongated slot in secondary platform 26, which is oval or eliptical, and the slot 28 is positioned along the longer axis of the elipse.

Figure 3:
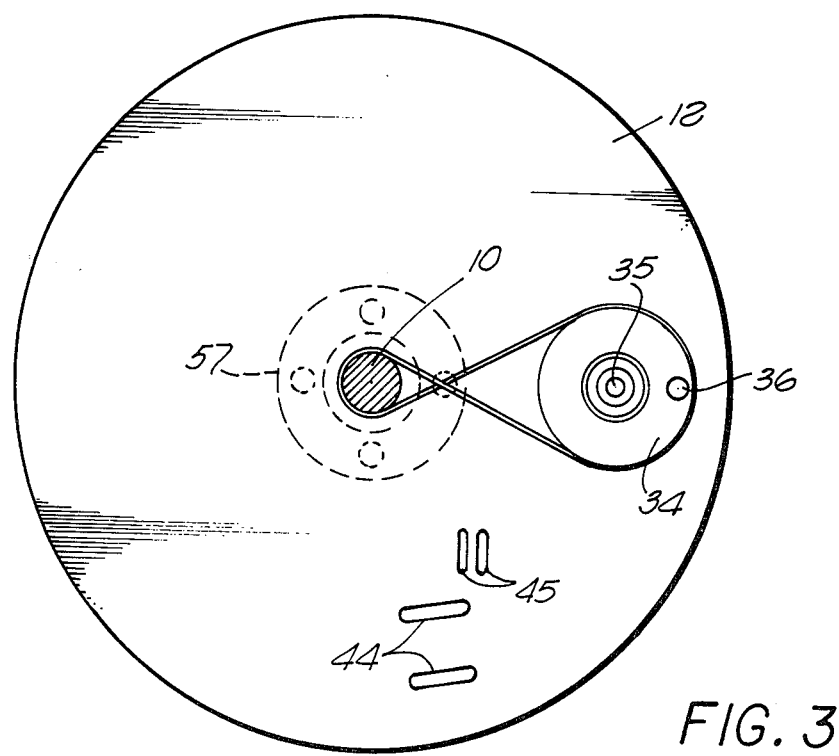
FIG. 3 is a plan view of the rotating platform of the apparatus which carries the light source and camera mechanism.
Figure 4:
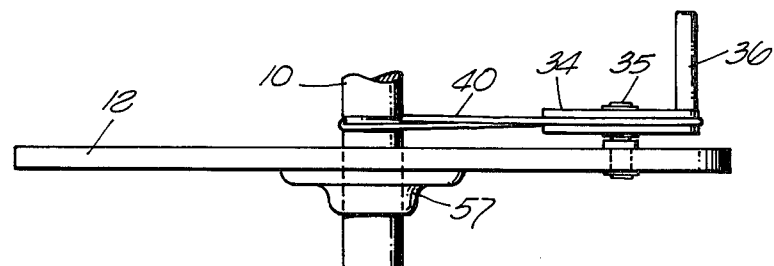
FIG. 4 is a side elevational view of the rotary platform and drive mechanism.

Number 34 designates a circular rotor having a shaft 35 upstanding perpendicularly from the platform 12, as may be seen in FIGS. 3 and 4, Number 36 designates a vertical post upstanding from the circular rotor 34 that is in an eccentric position. This post or stem 36 is adapted to engage the slot 28 whereby when the rotor 34 rotates the stem 36 in the slot 28 will cause the secondary platform 26 to oscillate for purposes as will be described. Number 40 designates a crossed belt which passes around the rotor 34 which is grooved to receive it, the belt 40 also passing around the column 10 as shown, whereby when the platform 12 is rotated by means of the motor 14, the rotor 34 is caused to rotate. As may be seen in FIG. 3 the platform 12 is provided with slots as shown at 44 for purposes of mounting the light source as will be described and also slots 45 for purposes of mounting the camera holder.

Figure 5:
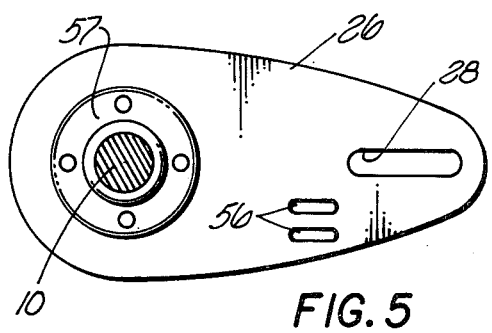
FIG. 5 is plan view of the secondary platform which carries the film holder and it driven to have relative movement.
Figure 6:
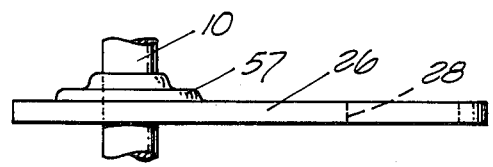
FIG. 6 is an elevational view of the secondary platform of FIG. 5.

Referring again to FIG. 1 the light source is designated by number 50 having mounting feet 51 and 52 whereby it is mounted in the slots 44 in platform 12. The light source 50 is shown more in detail in FIGS. 7, 8 and 9 which will be referred to again presently. It will be noted that FIG. 5 is a plan view of the secondary platform 26 showing the slot 28 and also slots 56 for mounting the film holder on the secondary platform and showing the bushing 57 through which the column 10 extends.

In FIG. 1 number 60 designates the film holder of the camera which is mounted on the secondary platform 26 by way of the slots 56 previously described. Number 62 designates a bellows extending between the film holder 60 and the camera lens 64 which is mounted on the side of the element 20 to receive a reflected beam of light. The reflected beam of light transmits an image in a rectangular pattern as identified by the letters ABCD on the film holder 60.

Figure 7:
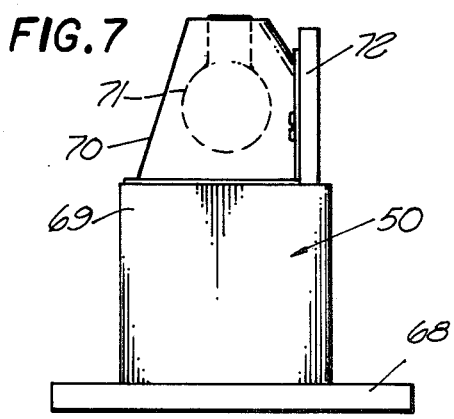
FIG. 7 is the side elevational view of a preferred form of light source.
Figure 9:
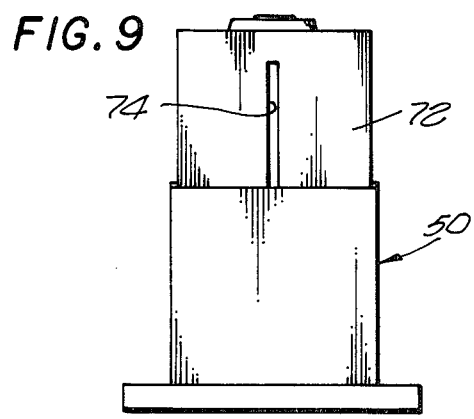
FIG. 9 is a front view of the light source of FIG. 7 and 8, showing the light emitting slot or slit.
Figure 8:
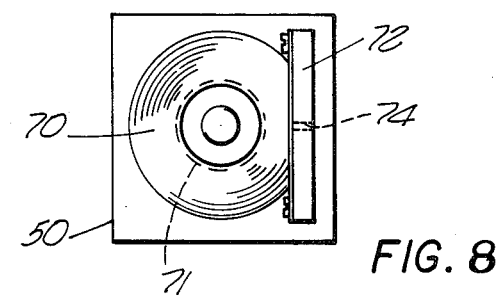
FIG. 8 is a plan view of the light source of FIG. 7.

As previously indicated, FIGS. 7, 8 and 9 show a preferred form of the light source 50. It comprises a base 68 and housing 69 over which is a circular shield element 70 in which is the light bulb source 71. At one side of the shield or reflector 70 is a flat shield 72 having a slot 74 so that the light is in the form of a beam passing through the slot 74, this beam being the reflected image which reflects onto the film holder and film plate in the area ABCD as described in connection with FIG. 1.

Figure 2:
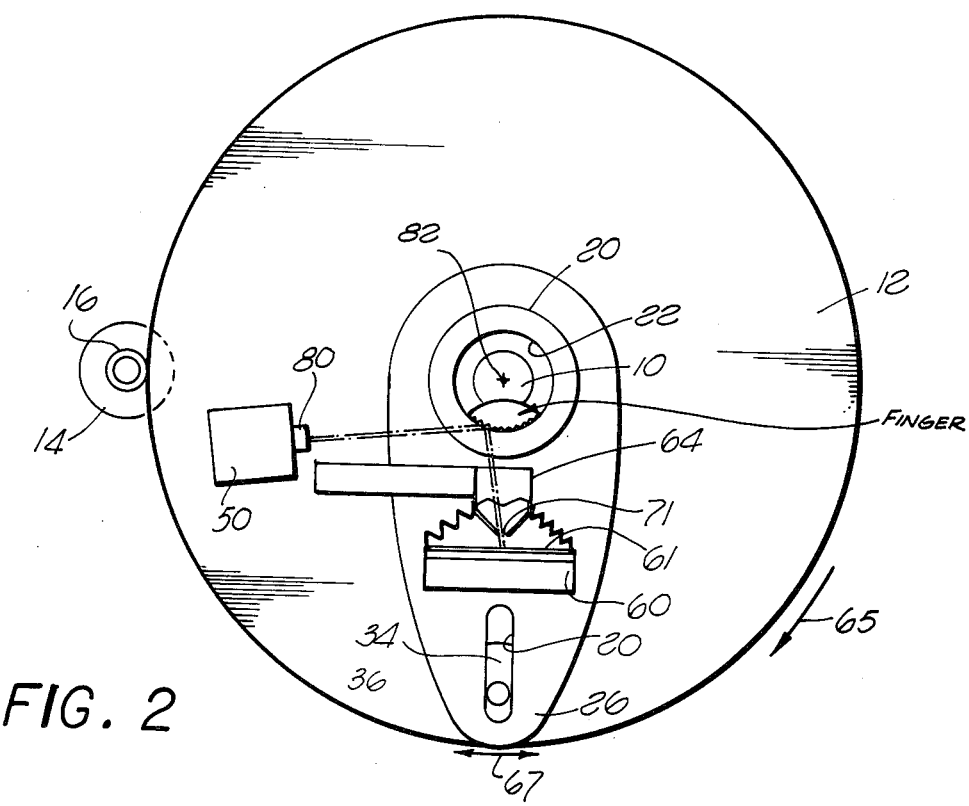
FIG. 2 is a diagramatic partial plan view of the apparatus of FIG. 1.

FIG. 2 is a plan view which show the relationship of parts as already described and illustrates the incident beam of light from the light source 50 which is reflected in the interior surface 22 of the element 20 to the lens system 64 supported by lens support 63 on movable carriage 12, in slots 45 and onto the film plate 61 mounted in film holder 60 which is supported on member 26. As may be seen in FIG. 2, the finger is placed onto the surface 22 of the opening or bore in the element 20 with the skin ridges against the interior surface 22 as shown. The light source 50 includes a light collimating part 80 and the light is in a beam having an angle of incidence against the skin ridges, as shown and an angle of reflection into the lens system 64 through slit 71 to reflect a beam image against the sensitive film plate 61. The platform 12 is rotated by motor 14 around the axis of rotation 82 with the source of illumination 50 on. The member 26, on which the film holder 60 and film plate 61 is mounted is rotated in the direction of the arrow 65 by the member 36 projecting into slot 28. Also, because of the eccentric mounting of pully 34 with respect to the axis 82, it is also simultaneously oscillated in the direction of the double ended arrow 67 with respect to the platform 12. The oscillation of the member 26 during rotation provides the desired scanning of the film plate 61 to record the finger print image thereon.

As an alternative to the sensitized film plate 61, sensitive electronic elements may be utilized and inserted for remote reading of the light reflections or the skin ridge patterns.

Depending on the amount of skin ridge coverage desired in the photograph, the assembly 12 may rotate from 0 degrees through 360 degrees. At the end of the pre set cycle of angular travel the means of illumination is turned off and assembly 12 returned to the starting position. The platform 12 may be rotated around the axis 82 by electrical or mechanical power means or by way of springs, levers or other means manipulated by the operator. The speed must be governed to be constant but may be adjustable to allow for various sensitized film plate speeds of development. By varying the angle of incidence of the reflected light the image reaching the sensitized film plate can result either in the valleys being shown as light and ridges being shown as dark or the reverse of this, that is, the valleys dark, and the ridges light.

Figure 10:
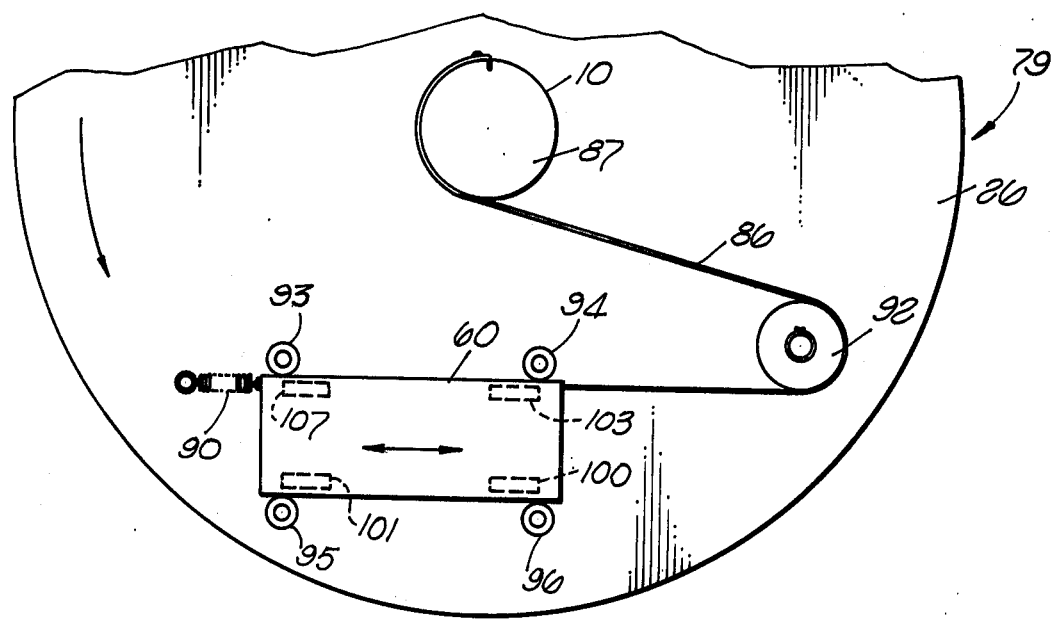
FIG. 10 is a partial schematic view of the sensitive film drive or transport showing its relative movements.
Figure 11:
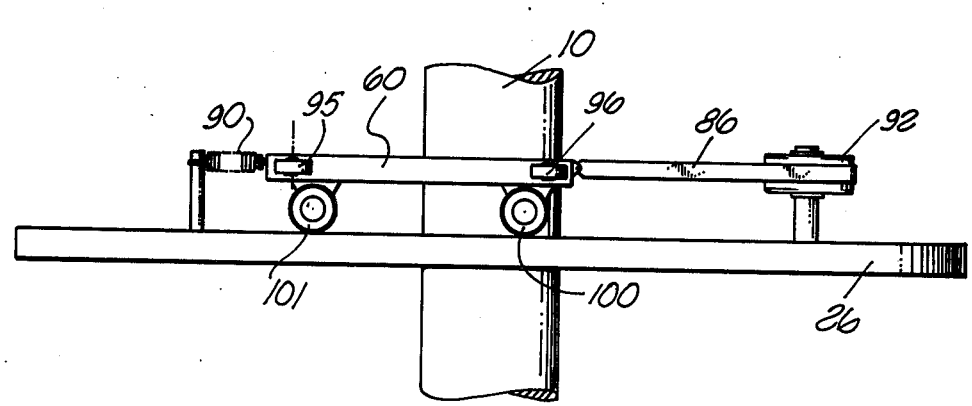
FIG. 11 is a side elevational view of the film transport mechanism of FIG. 10.

Thus the assembly as shown on the platform 12 rotates at a constant rate in the manner described. The sensitized film has relative movement on member 26 with respect to the lens system 64 and slit 71. This movement may also be provided by other means. FIGS. 10 and 11 illustrate another embodiment, generally designated 79 of the present invention to provide such relative movement.

As shown on FIGS. 10 and 11 a tape 86 is wrapped around pully 87, the pitch diameter of which is equal to the inside diameter of the optical element 20 and pully 87 is coupled to shaft 10. The pitch diameter of pully 87 is also concentric with the inside diameter of the optical element 20. Number 90 designates a spring which maintains tension on the tape 86 and therefore maintains the proper positioning of the film holder 60. It is to be understood that other mechanisms may be provided to perform this specific function.

Referring more in detail to FIGS. 10 and 11, secondary platform 26 can rotate about the column 10. Belt 86, one end of which is attached to the column 10 is wrapped around column 10. This effectively shortens the belt 86 during rotation of the platform 26 with respect to the platform 26. Film carrier 60 is attached to the belt 86 which passes around pulley 92 and is thus drawn across the platform 26 and is guided by the rollers 93, 94, 95 and 96 while traveling on four corner rollers 100, 101, 102 and 103. Guided by the rollers the film carrier 60 moves in a straight line with respect to the rotating platform 26 a distance proportional to the angular motion of the secondary platform 26. As may be seen, the sensitive film plate holder 60 remains in the same plane in the same relative oriented position with respect to the lens 64 and the reflected beam of light carrying the image of the skin ridges it is caused to scan by moving in the direction as described. In the embodiment of FIG. 1 this scanning is done by way of the rotor 34, pin 36 and slot 28 and in the alternative embodiment 79 of FIG. 10 and 11 is accomplished as described by means of the belt 86.

As an alternative to typical sensitized paper film, various types of such papers can be used such as particular type that is available and that is used in phototype setting.

From the foregoing it will be observed that the scanning is automatic. The apparatus may be automatic being started by way of a push button then continuing to run with the light source on or manipulations may be performed by the operator. Preferably the motor drives the scanning mechanism unitl the end of travel at which time the light source is turned off and motor reversed. The motor drives the scanning device back to the start.

Figure 12:
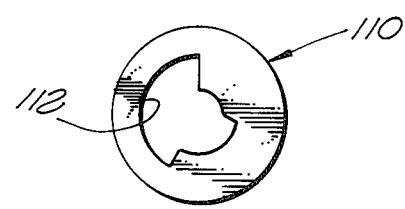
FIG. 12 is a detailed sectional view of a modified form of finger lens having a different shape or configuration of bore in it.

FIG. 12 shows a modified form of finger receiving element as designated at 110 and which does not have a circular bore but rather as a bore having configuration as illustrated at 112 and having several radii to accommodate to different size fingers. The proper radius can be presented to the rest of the mechanism properly by rotating the lens at the start of the operation.

OPERATION OF THE APPARATUS

From the foregoing description of the apparatus, the subassemblies and the components and the description of the operation of the components those skilled in the art may readily understand the over all operation and utilization of the apparatus. The finger is merely inserted in bore 22 of the element 20 and pressure may be exerted or means may be provided to exert pressure on the end of the finger. The objective is, of course, to produce an accurate and dependable skin ridge pattern that is the finger print of the finger that is inserted. During operation, the light source is, of course, ON directing its beam of light to the interior surface of the element 20 with the image of the skin ridges being reflected at the angle of reflection through the lens 64 and the slit to the rectangular area on the film plate 61. The main platform 12 rotates at a uniform rate carrying the light source and lens around the element 20 having the inserted finger therein. At the same time the film holder 60 is caused to scan by moving at a particular scanning rate related to the rate of angular movement of the platform 12 as described.

From the foregoing, those skilled in the art will fully understand and appreciate the nature of the construction of the invention and its utilization and the manner in which it achieves and realizes all of the objectives as set forth in the foregoing.

The foregoing disclosure is representative of the embodiments of the invention and is to be interpreted in an illustrative rather than in a limiting sense. The invention is to be accorded the full scope of the claims appended hereto.

I claim:
1. Apparatus for optically obtaining and recording skin ridge patterns comprising:
   an arcuate transparent, finger receiving member having an arcuate bore adapted to have a finger having skin ridge patterns thereon inserted therein;
   a light source positioned to transmit a beam of light to said finger receiving member and to be reflected therefrom from the interior surface thereon;
   a light sensitive film plate positioned in a plane to have the reflected beam of light impinged thereon; and
   motion producing means for producing first relative angular motion and second relative motion between said finger receiving member and said sensitive film plate.
2. The apparatus as defined in claim 1, and further comprising:
   a lens means intermediate said finger receiving member and said film plate;
   a platform means on which said light source and said lens means are mounted;
   said motion producing means further comprises first rotation means for rotating said platform angularly relative to said finger receiving member to provide said first relative angular motion.
3. The apparatus in claim 2, wherein said finger receiving member is cylindrical having a cylindrical bore and said first rotation means rotates said light source and said lens means about the axis of the finger receiving member.
4. The apparatus defined in claim 3, wherein said sensitive film plate lies in a plane, and said motion producing means further comprises drive means for causing scanning by moving said film plate in the direction of its plane to provide said second relative motion.
5. The apparatus in claim 4, and further comprising:
   a secondary platform on which said sensitive film plate is mounted, and said drive means for causing said secondary platform and said film plate to be moved relative to said lens means.
6. The apparatus in claim 5 and further comprising:
   a film carrier mounted for linear movement on said secondary platform;
   a center column rotatable concentrically with said axis of said finger receiving member; and
   a flexible member attached to said film carrier and to said center column in a manner whereby when center column rotates tension is inserted on said flexible member whereby to move said film carrier linearly with respect to said platform and proportionally to the angular movement of said center column.
7. The apparatus as in claim 5 wherein said platform, lens means, light source, secondary platform and sensitive film plate are all supported from an upright center support column.
8. The apparatus as defined in claim 4, and further comprising:
   a film carrier positioned to carry said sensitive film plate in a plane having a predetermined orientation with respect to both said lens means and said reflected light beam, said sensitive film plate remaining in the same orientation by rotation relative to the lens means to provide said second relative motion.

9. The apparatus as in claim 1, and further comprising means for securely holding the finger in the finger receiving member.

10. The apparatus as in claim 1, wherein said light source and said sensitive film plate have a predetermined relative oriented position with respect to the finger receiving member, and said predetermined oriented position is maintained while the light source and sensitive film plate rotate about the finger receiving element.

* * * * *